United States Patent
Haga et al.

(10) Patent No.: US 10,933,101 B2
(45) Date of Patent: Mar. 2, 2021

(54) FERMENTED PRODUCT AND PRODUCTION METHOD THEREFOR

(71) Applicant: YAMADA BEE COMPANY, INC., Okayama (JP)

(72) Inventors: Asami Haga, Okayama (JP); Madoka Isoe, Okayama (JP); Ayanori Yamaki, Okayama (JP); Yuka Kimura, Okayama (JP)

(73) Assignee: YAMADA BEE COMPANY, INC., Okayama (JP)

( * ) Notice: Subject to any disclaimer, the term of this patent is extended or adjusted under 35 U.S.C. 154(b) by 15 days.

(21) Appl. No.: 16/474,050

(22) PCT Filed: Dec. 21, 2017

(86) PCT No.: PCT/JP2017/046026
§ 371 (c)(1),
(2) Date: Jun. 26, 2019

(87) PCT Pub. No.: WO2018/123828
PCT Pub. Date: Jul. 5, 2018

(65) Prior Publication Data
US 2019/0365828 A1 Dec. 5, 2019

(30) Foreign Application Priority Data

Dec. 28, 2016 (JP) .............................. JP2016-255467

(51) Int. Cl.
| | | |
|---|---|---|
| *C12P 1/04* | (2006.01) |
| *A61K 35/644* | (2015.01) |
| *A23L 21/25* | (2016.01) |
| *A23L 33/105* | (2016.01) |
| *A61K 8/9789* | (2017.01) |
| *A61K 8/98* | (2006.01) |
| *A61K 8/99* | (2017.01) |
| *A61K 35/747* | (2015.01) |
| *A61K 36/28* | (2006.01) |
| *A61Q 19/00* | (2006.01) |
| *A61Q 19/08* | (2006.01) |

(52) U.S. Cl.
CPC ............ *A61K 35/644* (2013.01); *A23L 21/25* (2016.08); *A23L 33/105* (2016.08); *A61K 8/9789* (2017.08); *A61K 8/988* (2013.01); *A61K 8/99* (2013.01); *A61K 35/747* (2013.01); *A61K 36/28* (2013.01); *A61Q 19/00* (2013.01); *A61Q 19/005* (2013.01); *A61Q 19/007* (2013.01); *A61Q 19/08* (2013.01); *A23V 2002/00* (2013.01); *A23Y 2220/00* (2013.01)

(58) Field of Classification Search
CPC ........................................................ C12P 1/04
See application file for complete search history.

(56) References Cited

FOREIGN PATENT DOCUMENTS

| | | |
|---|---|---|
| CN | 103564592 A | 2/2014 |
| CN | 105076934 A | 11/2015 |
| CN | 105176770 A | 12/2015 |
| JP | H 07187991 A | 7/1995 |
| JP | 2010/525809 A | 7/2010 |
| JP | 2012/121871 A | 6/2012 |
| JP | 2014/028781 A | 2/2014 |
| JP | 2015/157772 A | 9/2015 |
| JP | 2015/223106 A | 12/2015 |
| JP | 5860577 B2 | 2/2016 |
| KR | 2016/0049812 A | 5/2016 |
| WO | WO 2008/136730 A1 | 11/2008 |
| WO | WO 2013/099883 A1 | 7/2013 |

OTHER PUBLICATIONS

English bibliographic information fo Nano S, KR 2006034522 A, 2006.*
International Search Report dated Mar. 27, 2018 for International Patent Application No. PCT/JP2017/046026, 3 pages.
International Preliminary Report on Patentability dated Jul. 11, 2019 for International Patent Application No. PCT/JP2017/046026, 10 pages.
Raga, et al: "Effects of fermented honey extracts on human skin", Abstracts of the Annual Meeting of the Pharmaceutical Society of Japan, Mar. 2017, vol. 137, p. 159 (26PB-pm071), with partial English translation.
Communication forwarding the extended European Search Report dated Aug. 5, 2020 for European Patent Application No. 17886586.1, 7 pages.
Bisson, et al: "The Two Faces of Lactobacillus kunkeei: Wine Spoilage Agent and Bee Probiotic", *Catalyst: Discovery Into Practice*, Jul. 8, 2016; vol. 1, No. 1, pp. 1-11, XP055718239.

* cited by examiner

*Primary Examiner* — Rosanne Kosson
(74) *Attorney, Agent, or Firm* — Squire Patton Boggs (US) LLP

(57) ABSTRACT

The present invention provides a fermented product obtained by fermenting honey and camomile or a treated product thereof with *Lactobacillus kunkeei*.

10 Claims, No Drawings

FERMENTED PRODUCT AND PRODUCTION METHOD THEREFOR

TECHNICAL FIELD

The present invention relates to a fermented product and a production method therefor.

BACKGROUND ART

It is known that the skin, especially the epidermis, has a barrier function. The barrier function is a function for preventing excessive water perspiration from the inside of the living body and the invasion of a foreign substance such as bacteria from the outside of the body. It is considered that a tight junction existing in the granular layer of the epidermis play an important role in the barrier function of the skin. Tight junctions not only closely join together adjacent cells but also seals between cells to control the permeation of a substance. It is claudin, occludin and tight junction proteins, which are cell membrane proteins, that constitute tight junctions. It is considered that these proteins constitute tight junction strand skeletons, and control the barrier function of tight junctions. In Patent Literature 1, a claudin-generating promoter and an occludin-generating promoter containing a plant extract are described. In Patent Literature 2, an agent for improving the skin barrier function, consisting of a cactus fruit extract obtained from fruits of a plant belonging to Cactaceae Opuntia is described.

CITATION LIST

Patent Literature

Patent Literature 1: JP 5860577B2
Patent Literature 2: JP 2012-121871A

SUMMARY OF INVENTION

Technical Problem

In Patent Literature 1, it is disclosed that the effect of promoting the generation of occludin was investigated by using a camomile extract. In Patent Literature 1, it is however shown that the camomile extract had little effect of promoting the generation of occludin.

An object of the present invention is to provide a new honey fermented product having an excellent skin-improving effect.

Solution to Problem

The present inventors have newly found that a fermented product obtained by fermenting honey and camomile or a treated product thereof using *Lactobacillus kunkeei* has an excellent skin-improving effect.

The present invention provides a fermented product obtained by fermenting honey and camomile or a treated product thereof with *Lactobacillus kunkeei*. The fermented product has an excellent skin-improving effect.

In the fermented product, it is preferable that the camomile or the treated product thereof be dry powder of camomile flowers. A fermented product having a higher skin-improving effect can be obtained more easily by using dry powder of camomile flowers.

In the fermented product, it is preferable that the mass ratio of the honey to the camomile or the treated product thereof be 26:1 to 4:1. When the mass ratio is in the range, a still higher skin-improving effect is obtained.

The fermented product is suitable for at least one selected from the group consisting of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin.

The present invention can also be considered as a fermented product for use in at least one selected from the group consisting of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin, wherein the fermented product is obtained by fermenting honey and camomile or a treated product thereof with *Lactobacillus kunkeei*.

The present invention can also be considered as at least one selected from the group consisting of a method for improving the skin barrier function, a method for moisturizing the skin, a method for improving the elasticity of the skin, a method for improving the dullness of the skin, a method for improving the wrinkle of the skin, a method for improving rough dry skin, a method for antiaging of the skin, a method for improving the texture of the skin, and a method for improving sensitive skin, each comprising a step of orally administering a fermented product obtained by fermenting honey and camomile or a treated product thereof with *Lactobacillus kunkeei* to a subject in need thereof; or a step of applying the fermented product to the skin of the subject.

The present invention can also be considered as the application of a fermented product obtained by fermenting honey and camomile or a treated product thereof with *Lactobacillus kunkeei* in the production of at least one selected from the group consisting of agents for improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin.

The present invention provides a food, a cosmetic, a drug or a quasi drug, comprising the fermented product.

The present invention provides a method for producing a fermented product, comprising a step of fermenting honey and camomile or a treated product thereof with *Lactobacillus kunkeei* to obtain a fermented product. The fermented product obtained by the production method has an excellent skin-improving effect.

In the production method, it is preferable that the camomile or the treated product thereof be dry powder of a camomile flower.

In the production method, it is preferable that the mass ratio of the honey to the camomile or the treated product thereof be 26:1 to 4:1.

The fermented product obtained in the production method is suitable for at least one selected from the group consisting of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin.

The present invention provides a method for producing a food, a cosmetic, a drug or a quasi drug, comprising a step of adding a fermented product obtained by the production method.

Advantageous Effects of Invention

A fermented product of the present invention has an excellent skin-improving effect.

DESCRIPTION OF EMBODIMENTS

Aspects for the embodiments of the present invention will be described in detail hereinafter. The present invention is not, however, limited to the following embodiments. "%" means "% by mass" herein unless otherwise specified.

A fermented product according to the present embodiment is obtained by fermenting honey and camomile or a treated product thereof (hereinafter also called "camomile material") with *Lactobacillus kunkeei*.

Honey is a product that honeybees have produced from syrup collected from nectar of plants, sap, secreting fluid of insects which are parasitic on plants, and the like as a main raw material. In the present embodiment, the type of raw material honey subjected to fermentation is not particularly limited and examples that can be used include manuka honey, acacia honey, honeydew honey, clover honey, orange honey, milk vetch honey, rosemary honey, sunflower honey, rape flower honey, coffee honey. Honey may be used alone or in combination of two or more. The type of honeybees used to collect honey and the producing district of honey are not particularly limited.

Camomile is a plant of *Compositae*, and the scientific name is *Matricaria chamomilla* L. Parts of camomile to be used are not particularly limited, and can be suitably selected, and examples thereof include a leave, a stalk, a root, a flower, a bud, a seed, a fruit, a peel, a putamen, a terrestrial part, the whole plant and a mixture of these. It is preferable that a part of camomile to be used be flowers.

The camomile material to be subjected to fermentation may be camomile itself obtained by collecting camomile, or may be the treated products of camomile. Examples of the camomile treated product include treated products obtained by subjecting camomile to treatment such as drying, pulverization and extraction. These treatments may be performed alone or in combination of two or more.

The camomile treated product may be, for example, a dried product, a pulverized product, a crushed product, powder, extract or the like of camomile. Camomile can be dried, for example, by solar drying, hot-air drying, freeze drying, spray drying or the like. Pulverization and crushing can be performed, for example, by using a grinder, a crusher and the like, respectively. It is preferable that the camomile material be dry powder of camomile. The dry powder of camomile can be obtained, for example, by drying and further pulverizing camomile. It is preferable that camomile be dried immediately after collection and pulverized. As the camomile treated product, commercial items can be used.

The extract of camomile can be obtained by extracting it from camomile by a method commonly used for plant extraction. For example, extraction parts of camomile which is an extraction raw material are fed to a treatment tank filled with an extracting solvent, soluble components are eluted while stirring optionally if needed, the mixture is then filtered to remove the extraction residue, and extract liquid can be obtained.

As the extract of camomile, extract liquid obtained by extracting from camomile may be used as it is, for example, and also a product of the extract of camomile further subjected to treatment such as dilution, concentration, drying, filtration or purification may be used.

The extracting solvent may be, for example, an aqueous solvent, a hydrophilic organic solvent or the like. Examples of the aqueous solvent include pure water, purified water, tap water, well water, mineral spring water, mineral water, hot spring water, spring water, fresh water, hot water, ion exchange water, physiological saline, a phosphate buffer and phosphate buffered saline. Examples of the hydrophilic organic solvent include lower alcohols having 1 to 5 carbon atoms such as methanol, ethanol, propyl alcohol and isopropyl alcohol; lower aliphatic ketones such as acetone and methyl ethyl ketone; and polyhydric alcohols having 2 to 5 carbon atoms such as 1,3-butylene glycol, propylene glycol and glycerin. These extracting solvents may be used alone or in combination of two or more.

Fermentation can be performed by using *Lactobacillus kunkeei*. It is preferable that *Lactobacillus kunkeei* used to obtain a fermented product according to the present embodiment shows assimilating ability for glucose and fructose, and it is preferable that it shows assimilating ability for glucose, fructose, sucrose, trehalose and gluconates. *Lactobacillus kunkeei* may be *Lactobacillus kunkeei* BPS402. *Lactobacillus kunkeei* BPS402 has been deposited with Patent Organism Depositary, National Institute of Advanced Industrial Science and Technology (Chuo 6th, Higashi 1-1-1, Tsukuba-shi, Ibaraki Prefecture, Japan (zip code 305-8566)) under accession No. FERM BP-22177 as of Oct. 3, 2011, and is available. The strain has been transferred to an international depositary now, and the accession No. is FERM BP-11439.

*Lactobacillus kunkeei* used for fermentation can be cultured according to a conventional method. As long as the bacterium can be cultured in a medium, the medium is not particularly limited, and a natural medium, a synthetic medium, a semisynthetic medium or the like can be used. A medium containing a nitrogen source and a carbon source can be used, examples of the nitrogen source include a meat extract, peptone, casein, a yeast extract, gluten, soybean flour, soybean hydrolysate and an amino acid, and examples of the carbon source include glucose, lactose, fructose, inositol, sorbitol, starch syrup, starch, malted rice liquid, wheat bran, bagasse and molasses. Inorganic matter (for example, ammonium sulfate, potassium phosphate, magnesium chloride, sodium chloride, calcium carbonate, iron, manganese, molybdenum), various vitamins or the like can be added besides.

The culture temperature may be, for example, 4 to 45° C., it is preferable that it be 25 to 40° C., and it is more preferable that it be 28 to 33° C. The culture period may be 8 to 72 hours. The culture may be performed by aeration shaking or aeration stirring. The pH of the medium may be, for example, 4.0 to 9.0, and it is preferable that it be 6.0 to 8.0. Examples of the culturing method include inoculating the bacterium into an MRS medium and culturing it at 30° C. for 48 hours. Bacterial liquid obtained by culturing *Lactobacillus kunkeei* may be inoculated into a fermentation medium containing honey and a camomile material as it is and used for fermentation, and it may be diluted with a medium or the like and used.

Honey and a camomile material can be fermented with *Lactobacillus kunkeei*, for example, at 4 to 45° C., and it is preferable to ferment them at 25 to 40° C. The fermentation time may be, for example, 12 to 60 hours, and it is preferable that it be 24 to 48 hours. The pH of the honey-containing product when fermentation starts may be, for example, 3 to 8, and it is preferable that it be 4 to 6. The fermentation may be performed by aeration shaking or aeration stirring.

Honey and a camomile material can be fermented by culturing *Lactobacillus kunkeei* in a fermentation medium containing honey and the camomile material. The fermentation medium containing honey and the camomile material may be in a form in which *Lactobacillus kunkeei* can ferment, and may be in a form such as a liquid, a paste or a gel. The fermentation medium may be honey and a camomile material dissolved or suspended in a solvent such as water.

The honey concentration in the fermentation medium when the fermentation starts may be, for example, 0.1 to 40%, 1 to 30%, or 8 to 13% based on the total amount of the fermentation medium. The honey concentration as a solid content in the fermentation medium when the fermentation starts may be, for example, 0.08 to 32%, 0.8 to 24%, or 6.4 to 10.4% based on the total amount of the fermentation medium.

The camomile material concentration as a solid content in the fermentation medium when the fermentation starts may be, for example, 0.01 to 20%, 0.1 to 5%, or 0.5 to 2% based on the total amount of the fermentation medium. The mass ratio of honey (total amount) to a camomile material (dry mass) in the fermentation medium when the fermentation starts may be, for example, 4000:1 to 1:200, or 26:1 to 4:1. The fermentation medium may further contain known nutrients required for the culture of lactic acid bacteria such as vitamins, amino acids, minerals, salts, surfactants, fatty acids, and metals. The honey to be used for fermentation may be subjected to sterilization treatment by heating or the like.

The fermented product according to the present embodiment may be a fermented product itself obtained by fermentation or may also be a product of the fermented product further subjected to treatment such as heating, filtration, purification, concentration, evaporation to dryness, freeze drying or spray drying. The fermented product according to the present embodiment may contain live body cells and/or dead body cells of *Lactobacillus kunkeei*, and body cells may be separated and removed by filtration or the like. Since the fermented product according to the present embodiment contains honey in the fermentation medium, it can be expected that components such as a vitamin and an amino acid will increase as compared with a raw material honey, and also can be expected that organic acids which is not contained in the raw material honey will be generated.

The fermented product according to the present embodiment has the effect of promoting the generation of at least one protein selected from the group consisting of occludin, claudin-1, claudin-4, tight junction protein-1, tight junction protein-2, tight junction protein-3, a type III collagen al chain, type IV collagen, aquaporin 3, serine palmitoyl transferase 2 and TIMP (tissue inhibitor of metalloproteinase) 2. The fermented product according to the present embodiment is accordingly suitable also for promoting the generation of occludin, claudin-1, claudin-4, tight junction protein-1, tight junction protein-2, tight junction protein-3, a type II collagen al chain, type IV collagen, aquaporin 3, serine palmitoyl transferase 2 and/or TIMP2. The fermented product is suitable also for promoting the expression of genes encoding these proteins.

The fermented product according to the present embodiment has the effect of suppressing the generation of at least one protein selected from the group consisting of interleukin-1α, interleukin-1β, cyclooxygenase 2 and matrix metalloprotease-9. The fermented product according to the present embodiment is accordingly suitable for suppressing the generation of interleukin-1α, interleukin-1β, cyclooxygenase 2 and/or matrix metalloprotease-9. The fermented product is suitable also for suppressing the expression of genes encoding these proteins.

The following is known as to the above-mentioned various proteins. Occludin, claudin-1, claudin-4, tight junction protein-1, tight junction protein-2, and tight junction protein-3 are tight junction-constituting proteins, and are supposed to participated in barrier function. Weak tight junctions cause increased water perspiration, the outflow of moisturizing components and calcium ions, poor synthesis of filaggrin and intercellular lipids relating to the amount of water in horny layers, keratin hyperplasia or the like, and lead to dry skin, sensitive skin, rough skin, the untransparency of the skin, the dullness of the skin, or the like. The effect of preventing dry skin, sensitive skin, rough skin and dullness, improving transparency, or the like can be expected by reinforcing tight junctions.

A large amount of type III collagen is contained in the embryonic skin, and plays a role in maintaining the elasticity of the skin. Type IV collagen is the main component of the basement membrane which exists between the epidermis and the dermis. Serine palmitoyl transferase 2 is the first rate-limiting enzyme when ceramide is synthesized. TIMP2 is an inhibitor of MMP (matrix metalloprotease).

It is known that interleukin-1α and interleukin-1β accelerate the activation of immune cells, and cause an inflammatory reaction. Especially interleukin-1α exists in keratinocytes in a large amount. It is known that cyclooxygenase 2 is a synthetase of prostaglandin, which relates to inflammation, and the expression increases by ultraviolet rays or the like. Reduction in the generation of cyclooxygenase 2 suppresses the generation of prostaglandin, which acts on melanocytes, and suppresses the generation of a spot by ultraviolet rays.

It is reported that MMP-9 decomposes basement membrane-constituting proteins, and the expression increases by ultraviolet rays. The prevention of an increase in MMP-9 suppresses the destruction of the basement membrane, and suppresses the formation of sagging and a wrinkle. The prevention of the destruction of the basement membrane prevents melanin formed in the epidermis from moving to the dermal side, and the generation of a persistent spot is suppressed thereby.

The fermented product according to the present embodiment is accordingly excellent in skin-improving effect, specifically, for example, the effects of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin. The fermented product according to the present embodiment is therefore, for example, suitable for at least one selected from the group consisting of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin. The antiaging of the skin includes, for example, the prevention or improvement of a wrinkle, the spot, the dullness, sagging, roughness or the like of the skin; or the improvement of the texture; or the like.

One embodiment of the present invention is a fermented product to be used for at least one selected from the group consisting of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin, wherein the fermented product is obtained by fermenting honey and camomile or a treated product thereof with *Lactobacillus kunkeei*.

One embodiment of the present invention is at least one selected from the group consisting of methods for improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin, comprising: a step of orally administering a fermented product obtained by fermenting honey and camomile or a treated product thereof with *Lactobacillus kunkeei* to a subject in need thereof; or a step of applying it to the skin of the subject.

One embodiment of the present invention is the application of a fermented product obtained by fermenting honey and camomile or a treated product thereof with *Lactobacillus kunkeei* in the production of at least one selected from the group consisting of agents for improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin.

The fermented product according to the present embodiment may be used as a cosmetic, a drug or a quasi drug as it is, and may be used as a component of a cosmetic, a drug or a quasi drug. A Cosmetic, a drug or a quasi drug may be, for example, in a form such as a solution, a milky lotion, an ointment, a cream, a paste, a jelly, an aerosol, powder, an oil, a solid or a foam. The fermented product may be applied directly to the skin by dropping, spraying, coating or the like, or may be orally administered. The fermented product according to the present embodiment may be a skin external preparation. Examples of the cosmetic or quasi drug include skin-care preparations such as face lotion, facial cleanser, milky lotion, cream, gel, essence, serum, a pack, a mask, cosmetic oil and ointment; makeup cosmetics such as foundation, a lipstick, cheek, rouge, eye shadow, eyeliner, mascara and face powder, facial cleanser; an agent for massage; an agents for cleansing; after shave lotion; pre shave lotion; shaving cream; body soap; body cream; soap; shampoo; rinse; a hair treatment agent; suntan lotion; sunscreen lotion; suntan cream; sunscreen cream; suntan gel; sunscreen gel; hair dressing; a hair tonic agent; a hair restorer; antiperspirant; a bath salt; a mouse rinse; and mouth wash.

When the fermented product according to the present embodiment is used as a component of a cosmetic, a drug, or a quasi drug, the content of the fermented product may be, for example, 0.01 to 100%, it is preferable that it be 0.1 to 50%, it is more preferable that it be 0.3 to 3.0%, and it is further preferable that it be 0.4 to 1.5% in a cosmetic, a drug, or a quasi drug.

When the fermented product according to the present embodiment is used as a component of a drug or a quasi drug, the drug or quasi drug may contain, for example, a pharmaceutically acceptable component (for example, a vehicle, a binding material, a lubricant, a disintegrator, an emulsifier, a surfactant, a base, a solubilizing agent and a suspending agent) as other components.

The drug or the quasi drug may be in any shape such as a solid, a liquid or a paste, and may be in a dosage form such as a tablet (including an uncoated tablet, a sugar-coated tablet, an effervescent tablet, a film-coated tablet, a chewable tablet, a troche agent or the like), a capsule, a pill, an epipastic (powdered drug), a fine granule, a granule, liquid medicine, a suspension, an emulsion, syrup, a paste, and an injection (including the case where it is blended in distilled water or infusion such as amino acid infusion or electrolyte infusion and prepared as liquid medicine at the time of use). These various preparations can be prepared, for example, by mixing the fermented product which is an active component, with other components if needed and forming into the above-mentioned dosage form.

The fermented product according to the present embodiment may be used as a food as it is, and may be used by adding it to the food. The above-described skin improvement can be expected by intake of the fermented product. Foods in which the tertiary function of foods (physical condition adjustment function) is emphasized are preferable. Examples of the food in which the tertiary function of the food is emphasized include a health food, a functional food, a nutritional composition, a nutritional supplement, a supplement, a food for health use, foods for specified health use, a functional nutritional food or a food with Function Claims.

When the fermented product is used by adding it to foods, foods may contain components accepted as foods. Examples of the components accepted as foods include minerals, vitamins, flavonoids, quinones, polyphenols, an amino acid, a nucleic acid, an essential fatty acid, a refrigerant, a binding agent, a sweetener, a disintegrator, a lubricant, a colorant, a flavor, a stabilizer, an antiseptic, a sustained release adjusting agent, a surfactant, a resolvent and a wetting agent.

Examples of the foods include the following, the fermented product is mixed into an intermediate product or a final product during processes for producing these, and foods to be used for the above-mentioned purposes can be obtained: beverages such as coffee, soft drinks such as juice and tea beverages, milk beverages, lactic acid bacteria beverages, yogurt beverages, carbonated beverages, alcoholic beverages such as a sake, a Western liquor, a fruit wine and a mead; spreads such as a custard cream; pastes such as a fruit paste; Western-style confectionery such as a chocolate, a doughnut, a pie, a cream puff, a gum, a jelly, a candy, a cookie, a cake and a pudding; Japanese-style confectionery such as a rice cake stuffed with sweet beans, a rice cake, a steamed bun, Castella, anmitsu, and a sweet jelly of adzuki beans; ices such as ice cream, popsicle and sherbet; precooked foods such as curry, a beef bowl, rice gruel, miso soup, soup, meat sauce, pasta, pickle, and jam; and seasonings such as dressing, a rice seasoning, a taste enhancer and instant soup.

A food, a cosmetic, a drug or a quasi drug consisting of the fermented product according to the present embodiment; or the food, cosmetic, drug or quasi drug comprising the fermented product is for at least one selected from the group consisting of improving the skin barrier function, moisturizing the skin, improving the elasticity of the skin, improving the dullness of the skin, improving the wrinkle of the skin, improving rough dry skin, antiaging of the skin, improving the texture of the skin, and improving sensitive skin. The above-mentioned food, cosmetic, drug, or quasi drug may be for promoting the generation of occludin, claudin-1, claudin-4, tight junction protein-1, tight junction protein-2, tight junction protein-3, a type III collagen α1 chain, type IV collagen, aquaporin 3, serine palmitoyl transferase 2 and/or TIMP2, and may be for promoting the expression of genes encoding these proteins. The above-mentioned food, cosmetic, drug, or quasi drug may be for suppressing the generation of interleukin-1α, interleukin-1β, cyclooxygenase 2 and/or matrix metalloprotease-9, and may be for suppressing the expression of genes encoding these proteins.

A food, a cosmetic, a drug or s quasi drug consisting of or comprising a fermented product according to the present embodiment may have, for example, claims such as improving a tight junction; improving the permeability of a paracellular route; fair skin; moisturizing the skin; preventing decrease in the elasticity and resilience of the skin, the dryness of the skin, rough dry skin, a wrinkle and aging; tightening the skin; improving the texture and the dullness of the skin; improving sensitive skin; and preventing photoaging. Preventing photoaging specifically means preventing or improving symptoms such as a spot and a wrinkle by the influence of light such as ultraviolet rays.

EXAMPLES

The present invention will be described based on Examples more specifically hereinafter. The present invention is not however limited to the following Examples.

[Preparation of Fermented Liquid of Honey and Camomile Flower Powder]

An aqueous solution (pH 5) containing 10% (w/w) acacia honey from Romania (Yamada Bee Company, Inc.) and 1% (w/w) camomile flower powder was prepared. The aqueous solution was treated at 110° C. for 5 minutes and sterilized to obtain a pre-fermentation liquid.

*Lactobacillus kunkeei* BPS402 was subjected to stationary culture on an MRS agar medium at 30° C. for 48 hours. A pre-culture solution was obtained by inoculating a loopful of bacteria from the formed colonies into 50 mL of the pre-fermentation liquid and subjecting it to shaking culture at 30° C. for 24 hours.

1 mL of the pre-culture solution was inoculated into 1000 mL of the fermentation substrate-containing liquid, and shaking culture was performed at the optimum temperature for 24 hours. The obtained fermented liquid was sterilized for 5 minutes at 110° C., and then filtered, and phenoxyethanol is added so that it is at a concentration of 0.5% of phenoxyethanol to obtain a fermented liquid of honey and camomile flower powder for tests.

[DNA Microarray Test]

DNA microarray tests were performed by using a human skin three-dimensional model kit (EFT-412, manufactured by KURABO INDUSTRIES LTD.). In accordance with the protocol, the skin model was moved to a 6-well plate and pre-cultured at 37° C. under 5% $CO_2$ overnight by using an assay medium. After pre-culture, 200 μL of the fermented liquid was added to the horny layer side, 2.5 ml of the assay medium were added to the dermal side, and the culture was continued for 3 days. After the culture, the skin tissues were washed with PBS (−), and DNA microarray analysis was performed after the tissues were collected by using Dermapunches (8 mm in diameter). Analysis was performed in the same way by using purified water to which 0.5% phenoxyethanol was added as a control. The cytotoxicity of the test substance to the skin three-dimensional model was evaluated by the MTT method.

Comprehensive analysis was performed as to 42450 genes, so that genes which increased 1.5 or more times in expression were 3012 genes, and genes which decreased to ½ or less in expression were 2826 genes by fermented liquid treatment as compared with the control. Genes encoding 15 proteins as shown in Table 1 were sampled among these as genes relating to the skin function. The cytotoxicity of the fermented liquid was not observed.

TABLE 1

| | Protein (gene) | Ratio of gene expressed (ratio to control) |
|---|---|---|
| Increase | Occludin (OCLN) | 12.01 |
| | Claudin 1 (CLDN1) | 3.67 |
| | Claudin 4 (CLDN4) | 21.65 |
| | Tight junction protein 1 (TJP1) | 1.82 |
| | Tight junction protein 2 (TJP2) | 10.83 |
| | Tight junction protein 3 (TJP3) | 8.33 |
| | Type III collagen α1 chain (COL3A1) | 2.18 |
| | Type IV collagen α1 chain (COL4A1) | 1.59 |
| | Aquaporin 3 (AQP3) | 2.14 |
| | Serine palmitoyl transferase 2 (SPTLC2) | 1.84 |
| | Tissue inhibitor of metalloproteinase 2 (TIMP2) | 1.83 |
| Decrease | Interleukin 1α (IL1A) | 0.31 |
| | Interleukin 1β (IL1B) | 0.13 |
| | Cyclooxygenase 2 (PTGS2) | 0.38 |
| | Matrix metalloprotease 9 (MMP-9) | 0.23 |

As shown in Table 1, by using the fermented liquid of honey and camomile flower powder, it was observed that the expression significantly increase 1.5 times or more as compared with purified water on genes coding proteins, such as a tight junction-constituting protein, a collagen, aquaporin 3 and a ceramide synthesis rate-limiting enzyme, which participate in improvement in moisture retention or a barrier function of the skin. Meanwhile, it was observed that the fermented liquid of honey and camomile flower powder significantly suppressed the expression as to the genes encoding interleukin 1, which participates in inflammatory reaction, cyclooxygenase-2, which was reported to increase by ultraviolet rays, and MMP-9, which decomposed protein which constituted the skin basement membrane.

[Test of Promotion of Protein Generation]

The fermented liquid of honey and camomile flower powder, and 10% honey water (10% acacia honey from Romania and 90% purified water) were used as test substances. Aqueous solutions in which the concentrations of these test substances were adjusted to 1.0% or 0.5% were further used for the following tests.

<Test of Promotion of Occludin Generation>

Normal human newborn infant epidermal keratinocytes (NHEKs) were cultured by using a normal human epidermal keratinocyte growth medium (KGM), and the cells were then collected by trypsin treatment. The collected cells were diluted with KGM to a concentration of $2 \times 10^5$ cells/ml, the diluted cells were then inoculated on a 96-well plate in an amount of 100 μL per well, and the inoculated cells were cultured overnight. After the culture, 100 μL of the test sample dissolved in KGM was added to each well, and the cells were cultured for 24 hours. After the culture, the medium was removed, and the amount of occludin expressed on the surfaces of the cells was measured by ELISA using a polyclonal anti-human occludin antibody with the cells fixed to the plate. A method for calculating the promotion ratio of occludin generated is as follows. The result is shown in Table 2.

Promotion ratio of occludin generated (%)=$A/B \times 100$

A: Absorbance at a wavelength of 405 nm when the test sample was added

B: Absorbance at a wavelength of 405 nm when the test sample was not added (control)

TABLE 2

| Concentration (%) | Test sample Promotion ratio of occludin generated (%) (control = 100) | |
|---|---|---|
| | Fermented liquid of honey and camomile flower powder | 10% honey water |
| 0.5 | 118.5 ± 2.0*** | 101.7 ± 1.1 |
| 1.0 | 112.4 ± 1.6*** | 104.5 ± 1.2* |

Mean ± S.E.,
n = 6,
*p < 0.05,
***p < 0.001

A high effect of promoting occludin generation was observed in the fermented liquid of honey and camomile flower powder at concentrations of 0.5% and 1.0%.

<Test of Promotion of Claudin-4 Generation>

Normal human newborn infant epidermal keratinocytes (NHEKs) were cultured by using a normal human epidermal keratinocyte growth medium (KGM), and the cells were then collected by trypsin treatment. The collected cells were diluted with KGM to a concentration of $2\times10^5$ cells/ml, the diluted cells were then inoculated on a 96-well plate in an amount of 100 μL per well, and the inoculated cells were cultured overnight. After the culture, 100 μL of the test sample dissolved in KGM was added to each well, and the cells were cultured for 24 hours. After the culture, the medium was removed, and the amount of claudin-4 expressed on the surfaces of the cells was measured by ELISA using a monoclonal anti-human claudin-4 antibody with the cells fixed to the plate. A method for calculating the promotion ratio of claudin-4 generated is as follows. The result is shown in Table 3.

Promotion ratio of claudin-4 generated (%)=$A/B\times100$

A: Absorbance at a wavelength of 405 nm when the test sample was added
B: Absorbance at a wavelength of 405 nm when the test sample was not added (control)

TABLE 3

| Concentration (%) | Test sample Promotion ratio of claudin-4 generated (%) (control = 100) | |
|---|---|---|
| | Fermented liquid of honey/camomile flower powder | 10% honey water |
| 0.5 | 104.5 ± 0.8** | 96.3 ± 1.2 |
| 1.0 | 103.0 ± 0.7* | 98.6 ± 1.1 |

Mean ± S.E.,
n = 6,
*p < 0.05,
**p < 0.01

The effect of promoting claudin-4 generated was observed in the fermented liquid of honey and camomile flower powder at concentrations of 0.5% and 1.0%.

<Test of Promotion of Tight Junction Protein-2 Generation>

Normal human newborn infant epidermal keratinocytes (NHEKs) were cultured by using a normal human epidermal keratinocyte growth medium (KGM), and the cells were then collected by trypsin treatment. The collected cells were diluted with KGM to a concentration of $2\times10^5$ cells/ml, the diluted cells were then inoculated on a 96-well plate in an amount of 100 μL per well, and the inoculated cells were cultured overnight. After the culture, 100 μL of the test sample dissolved in KGM was added to each well, and the cells were cultured for 24 hours. After the culture, the medium was removed, and the amount of ZO-2 expressed on the surfaces of the cells was measured by ELISA using a polyclonal anti-human ZO-2 antibody with the cells fixed to the plate. Tight junction protein-2 is also called ZO-2. A method for calculating the promotion ratio of ZO-2 generated is as follows. The result is shown in Table 4.

Promotion ratio of ZO-2 generated (%)=$A/B\times100$

A: Absorbance at a wavelength of 405 nm when the test sample was added
B: Absorbance at a wavelength of 405 nm when the test sample was not added (control)

TABLE 4

| Concentration (%) | Test sample Promotion ratio of ZO-2 generated (%) (control = 100) | |
|---|---|---|
| | Fermented liquid of honey/camomile flower powder | 10% honey water |
| 0.5 | 107.8 ± 2.1* | 101.2 ± 2.3 |
| 1.0 | 101.7 ± 2.1 | 100.8 ± 0.8 |

Mean ± S.E.,
n = 6,
*p < 0.05

The effect of promoting ZO-2 generated was observed in the fermented liquid of honey and camomile flower powder at a concentration of 0.5%.

As mentioned above, the effects of promoting occludin and claudin-4 generation were observed at concentrations of 0.5% and 1.0%, and the effects of promoting ZO-2 generation were observed at a concentration of 0.5% in the fermented liquid of honey and camomile flower powder. Meanwhile, although 10% honey water increased occludin generation at a concentration of 1.0%, it did not affect the amounts of claudin-4 and ZO-2 generated.

The invention claimed is:

1. A fermented product obtained by fermenting honey and camomile or a treated product of camomile with *Lactobacillus kunkeei*, wherein the treated product of camomile is at least one selected from the group consisting of a dried form, crushed form, powder and extract.

2. The fermented product according to claim 1, wherein the camomile or the treated product thereof is dry powder of a camomile flower.

3. The fermented product according to claim 1, wherein a mass ratio of the honey to the camomile or the treated product thereof is 26:1 to 4:1.

4. A composition comprising the fermented product according to claim 1, wherein the fermented product is present in at least a therapeutically effective amount, and wherein the composition is for at least one purpose selected from the group consisting of improving skin barrier function, moisturizing skin, improving elasticity of skin, improving dullness of skin, improving a wrinkle of skin, improving rough dry skin, antiaging of skin, improving texture of skin, and improving sensitive skin.

5. A food, a cosmetic, or a drug, comprising at least a therapeutically effective amount of the fermented product according to claim 1.

6. A method for producing the fermented product of claim 1, comprising a step of fermenting honey and camomile or a treated product of camomile with *Lactobacillus kunkeei* to obtain the fermented product.

7. The production method according to claim 6, wherein the camomile or the treated product thereof is dry powder of a chamomile flower.

8. The production method according to claim 6, wherein a mass ratio of the honey to the camomile or the treated product thereof is 26:1 to 4:1.

9. The production method according to claim 6, wherein the fermented product is added in at least a therapeutically effective amount to a composition, and wherein the composition is for at least one purpose selected from the group consisting of improving skin barrier function, moisturizing skin, improving elasticity of skin, improving dullness of skin, improving a wrinkle of skin, improving rough dry skin, antiaging of skin, improving texture of skin, and improving sensitive skin.

10. A method for producing a food, a cosmetic, or a drug, comprising a step of adding at least a therapeutically effective amount of the fermented product obtained by the production method according to claim 6 to a composition that is a food, cosmetic or drug.

\* \* \* \* \*